(12) United States Patent
Tsukada et al.

(10) Patent No.: US 10,918,334 B2
(45) Date of Patent: *Feb. 16, 2021

(54) WEARABLE ELECTRODE

(71) Applicants: NIPPON TELEGRAPH AND TELEPHONE CORPORATION, Tokyo (JP); TORAY INDUSTRIES, INC., Tokyo (JP)

(72) Inventors: Shingo Tsukada, Atsugi (JP); Nahoko Kasai, Atsugi (JP); Koji Sumitomo, Atsugi (JP); Hiroshi Nakashima, Atsugi (JP); Masanobu Sato, Tokyo (JP); Toru Arakane, Tokyo (JP); Yuri Hamano, Tokyo (JP); Keiji Takeda, Otsu (JP); Noriko Nagai, Otsu (JP); Takashi Teshigawara, Tokyo (JP)

(73) Assignees: NIPPON TELEGRAPH AND TELEPHONE CORPORATION, Tokyo (JP); TORAY INDUSTRIES, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/578,862

(22) PCT Filed: Jul. 8, 2016

(86) PCT No.: PCT/JP2016/070267
§ 371 (c)(1),
(2) Date: Dec. 1, 2017

(87) PCT Pub. No.: WO2017/007016
PCT Pub. Date: Jan. 12, 2017

(65) Prior Publication Data
US 2018/0296160 A1    Oct. 18, 2018

(30) Foreign Application Priority Data
Jul. 8, 2015 (JP) .............................. JP2015-137288

(51) Int. Cl.
*A61B 5/00* (2006.01)
*A61B 5/0408* (2006.01)

(52) U.S. Cl.
CPC .......... *A61B 5/6805* (2013.01); *A61B 5/0408* (2013.01); *A61B 2562/0209* (2013.01); *A61B 2562/222* (2013.01)

(58) Field of Classification Search
CPC ... A61B 5/6802; A61B 5/6804; A61B 5/6805; A61B 5/04; A61B 5/0402; A61B 5/0408;
(Continued)

(56) References Cited

U.S. PATENT DOCUMENTS 6,668,380 B2   12/2003   Marmaropoulos et al.
7,395,106 B2   7/2008    Ryu et al.
(Continued)

FOREIGN PATENT DOCUMENTS

CN   103930612 A   7/2014
CN   203914907 U   11/2014
(Continued)

OTHER PUBLICATIONS

ANSI/AAMI EC12:2000 (R2010), "Disposable ECG electrodes".
(Continued)

*Primary Examiner* — Eun Hwa Kim
(74) *Attorney, Agent, or Firm* — Harness, Dickey & Pierce, P.L.C.

(57) ABSTRACT

A wearable electrode includes: a garment including an outer member and a backing member configured to cover at least a part of an inner surface of the outer member; and an electrode unit configured to come into contact with a living body clothed in the garment to acquire a biological signal emitted by the living body and attached to an opposite side of the backing member from the outer member. The outer member and the backing member are connected to each
(Continued)

other in a part other than a part of the backing member, to which the electrode unit is attached.

3 Claims, 5 Drawing Sheets

(58) Field of Classification Search
CPC .... A61B 5/6823; A61B 5/6837; A61B 5/6849
See application file for complete search history.

(56) References Cited

U.S. PATENT DOCUMENTS

| | | | |
|---|---|---|---|
| 7,966,052 | B2 | 6/2011 | DeFusco et al. |
| 8,506,350 | B1* | 8/2013 | Silverman ............... A41C 3/00 450/67 |
| 8,527,028 | B2* | 9/2013 | Kurzweil ............ A61B 5/0408 600/382 |
| 2005/0034485 | A1 | 2/2005 | Klefstad-Sillonville et al. |
| 2007/0038057 | A1 | 2/2007 | Nam et al. |
| 2007/0073131 | A1 | 3/2007 | Ryu et al. |
| 2008/0287769 | A1* | 11/2008 | Kurzweil ............ A61B 5/0408 600/388 |
| 2008/0287770 | A1 | 11/2008 | Kurzweil et al. |
| 2013/0041272 | A1 | 2/2013 | Guillen Arredondo et al. |
| 2013/0281816 | A1 | 10/2013 | Strauss et al. |
| 2014/0039292 | A1 | 2/2014 | Su et al. |
| 2014/0343392 | A1* | 11/2014 | Yang ................ A61B 5/04011 600/393 |
| 2015/0025354 | A1 | 1/2015 | Salonius et al. |
| 2015/0119677 | A1* | 4/2015 | Liu .................... A61B 5/04085 600/389 |

FOREIGN PATENT DOCUMENTS

| | | |
|---|---|---|
| EP | 1506738 A1 | 2/2005 |
| EP | 2684516 A1 | 1/2014 |
| WO | WO-2012/088398 A2 | 6/2012 |

OTHER PUBLICATIONS

International Search Report for PCT/JP2016/070267, ISA/JP, dated Oct. 4, 2016, with English translation attached.
Extended European Search Report in related Application EP16821484. 9, ISA/EP, Munich, dated Oct. 18, 2018.
ANSI/AAMI EC12:2000/(R)2005, "Disposable ECG electrodes".
International Search Report for PCT/JP2016/070271, ISA/JP, Tokyo, dated Sep. 27, 2016.
Extended European Search Report in related application EP 16821485. 6, ISA/EP, Munich, dated Oct. 26, 2018.
Office Action for Chinese Application No. 201680036998.8; dated Nov. 29, 2019; 11 pages.
U.S. Notice of Allowance from counterpart U.S. Appl. No. 15/577,696, dated Jul. 24, 2020.

\* cited by examiner

WEARABLE ELECTRODE

CROSS-REFERENCE TO RELATED APPLICATIONS

This application is a 371 U.S. National Stage of International Application No. PCT/JP2016/070267, filed Jul. 8, 2016, which claims the benefit of and priority to Japanese Patent Application No. 2015-137288, filed Jul. 8, 2015. The disclosures of the above applications are incorporated herein by reference.

TECHNICAL FIELD

The present invention relates to a wearable electrode.

BACKGROUND ART

Research and development of systems in which electrode units are attached to undergarment type garments worn by users (living bodies) and biological signals emitted by the users are acquired have been actively underway as effective tools of medical care health systems for aging populations. Hereinafter, an object constituted of electrode units and garments is referred to as a wearable electrode.

Wearable electrodes require variations in undergarments according to sex, body shape, seasonal adaptations, size development, age, and the like. However, the number of pharmacist certification numbers increases for the various variations, and procedures become complicated due to the various variations, that is, it becomes difficult to approve, manufacture, and manage wearable electrodes as medical instruments. For this reason, the various requirements or the like need to be dealt with using as few wearable electrode variations as possible.

Also, in medical wearable electrodes, electrode units and wiring sections are determined by medical standards (for example, refer to Non-Patent Document 1).

DOCUMENTS OF THE PRIOR ART

Patent Document

Non-Patent Document 1

ANSI/AAMI EC12:2000 (R2010), "Disposable ECG electrodes"

SUMMARY OF INVENTION

Problems to be Solved by the Invention

However, when a garment moves due to a motion or the like of a user, there is a problem in that an electrode unit moves and thus measurement cannot be stably performed.

The present invention was made in view of the above-described circumstances, and an objective thereof is to provide a wearable electrode in which movement of an electrode unit is suppressed even when a garment worn by a user moves.

Means for Solving the Problems

An aspect of the present invention is a wearable electrode including: a garment including an outer member and a backing member configured to cover at least a part of an inner surface of the outer member; and an electrode unit configured to come into contact with a living body clothed in the garment to acquire a biological signal emitted by the living body and attached to an opposite side of the backing member from the outer member, wherein the outer member and the backing member are connected to each other in a part other than a part of the backing material to which the electrode unit is attached.

As a preferred example, the wearable electrode may include a wiring section disposed between the outer member and the backing member, wherein: a convex section is provided on one of the electrode unit and the wiring section to which a locking section formed of a material with conductivity is electrically connected; a concave section detachably locked to the convex section is provided on the other of the electrode unit and the wiring section to which a locked section formed of a material with conductivity is electrically connected; the locking section and the locked section are electrically connected to each other when the locking section and the locked section are locked to each other; and the convex section of the locking section is inserted into a slit formed in the backing member.

In this case, the wearable electrode may include: a wire holding section provided on the outer member or the backing member above the slit and configured to hold the wiring section.

As a preferred example, an outer member neckline section and a pair of outer member neckline sections may be provided on the outer member at a position to avoid a region having movement which is relatively larger than those of other regions when a user clothed in the garment moves his or her neck or arms, and a backing member neckline section and a pair of backing member neckline sections may be provided on the backing member at a position to prevent a region from having movement which is relatively larger than those of other regions when the user clothed in the garment moves his or her neck or arms.

In this case, preferably, elongation percentages in vertical and horizontal directions measured based on the standard of a JIS L 1096 8.16.1 A method in a sandwiched part sandwiched between the backing member neckline section and the pair of backing member neckline sections in a part which is the front of the user clothed in the garment in the backing member may be smaller than elongation percentages in the vertical and horizontal directions of parts of the backing member other than the sandwiched part.

Advantageous Effects of the Invention

According to the present invention, movement of an electrode unit can be suppressed even when a garment worn by a user moves.

EMBODIMENTS FOR CARRYING OUT THE INVENTION

An embodiment of a wearable electrode according to the present invention will be described below with reference to FIGS. 1 to 7.

Figure 1:
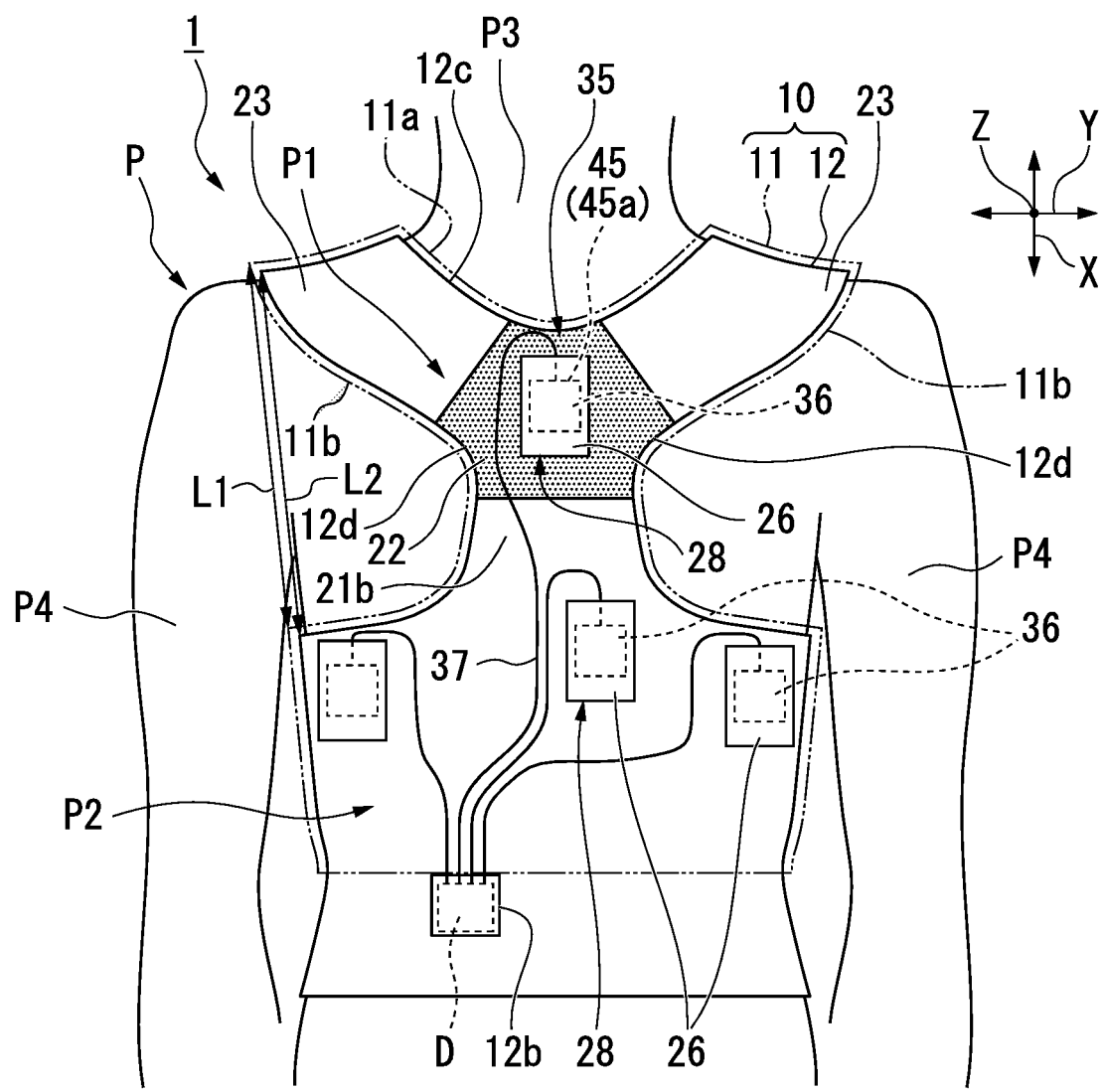
FIG. 1 is a front view of a wearable electrode according to an embodiment of the present invention.
Figure 2:
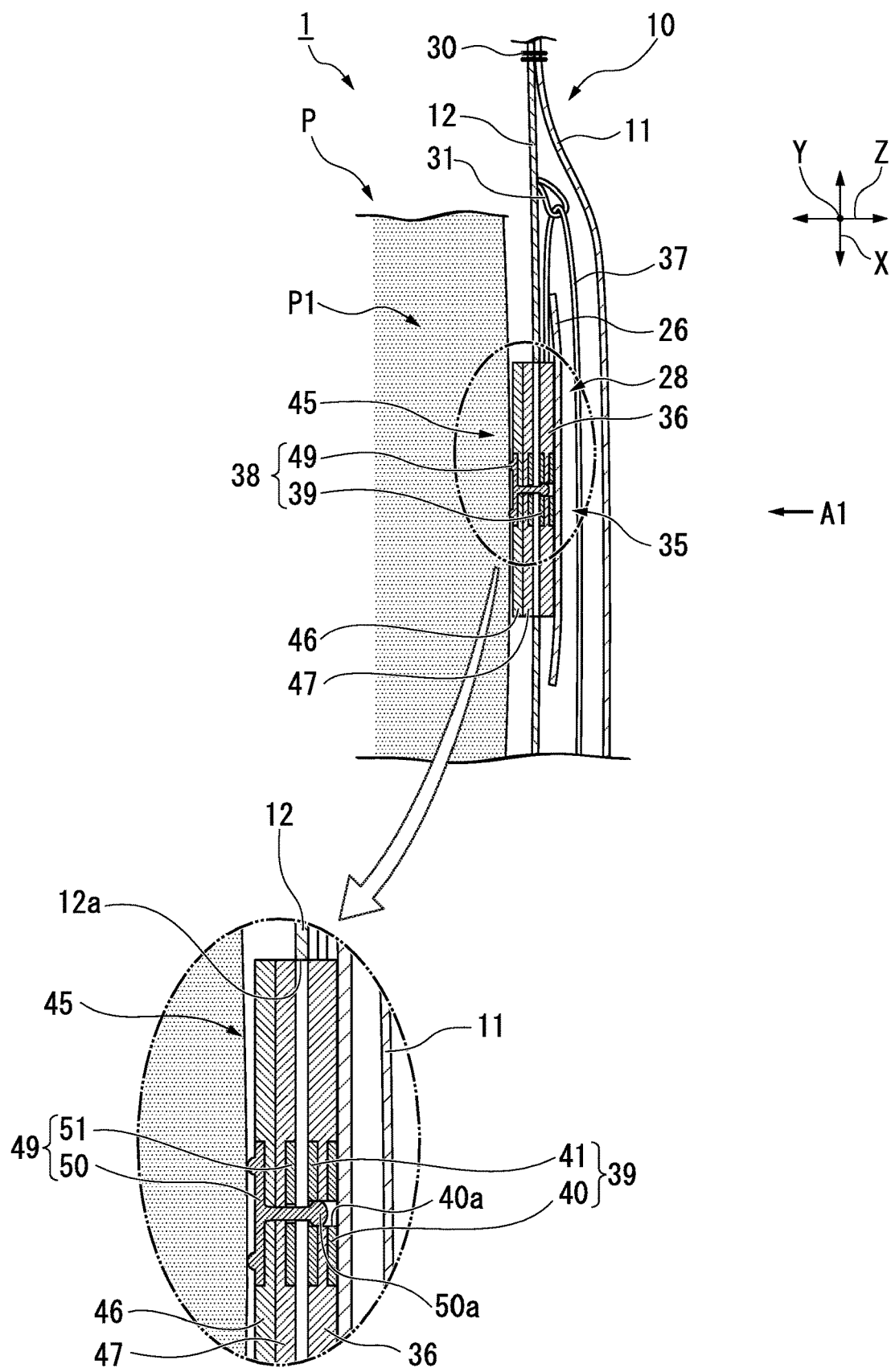
FIG. 2 is a vertical cross-sectional view of a front surface of the wearable electrode.

As shown in FIGS. 1 and 2, a wearable electrode 1 according to the embodiment includes an undergarment (a garment) 10 having an outer member 11 and a backing member 12, a wiring section 35 disposed between the outer member 11 and the backing member 12, and electrode units 45 attached to an opposite side of the backing member 12 from the outer member 11.

Note that FIG. 1 illustrates the outer member 11 indicated by an alternate long and two short dashed line.

First, the electrode units 45 will be described below.

Figure 3:
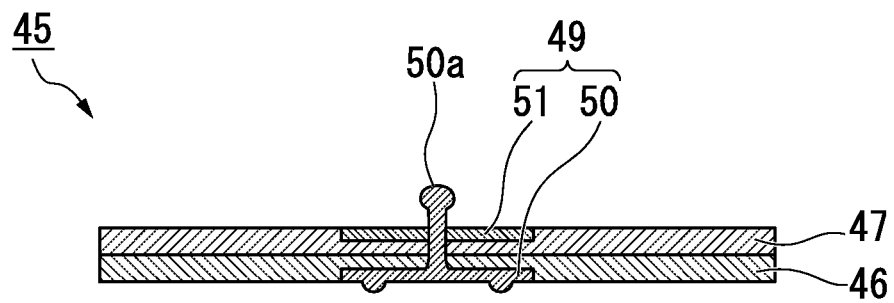
FIG. 3 is a cross-sectional view of an electrode unit of the wearable electrode.
Figure 3:
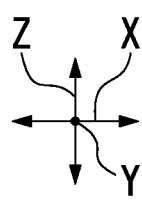

As shown in FIGS. 2 and 3, each of the electrode units 45 includes an electrode 46 formed in a flat plate shape and a waterproof layer 47 stacked on the electrode 46.

The electrode 46 is formed of a conductive fiber structure obtained by impregnating a fiber structure as a foundation cloth serving as a cloth which is a base thereof with conductive polymers.

Examples of a form of the fiber structure used for the electrode 46 include woven fabrics, knitted fabrics, and nonwoven fabrics. When the amount of conductive resins (conductive polymers) to be impregnated into the fiber structure is insufficient, since washing durability in repeated use is not obtained, the base weight of the fiber structure (a unit weight of the foundation cloth) is preferably 50 g/m$^2$ or more and 300 g/m$^2$ or less. When the base weight is less than 50 g/m$^2$, the amount of the impregnated conductive resin decreases and thus washing durability cannot be obtained. When the base weight is more than 300 g/m$^2$, the wearability is worse. The base weight is more preferably 60 g/m$^2$ or more and 250 g/m$^2$ or less.

The thickness of the fiber structure is preferably 0.2 mm or more and 2.0 mm or less. When the thickness is less than 0.2 mm, since the cloth is too thin, a substantial based weight decreases and thus the amount of the impregnated conductive resin decreases. When the thickness exceeds 2.0 mm, since the cloth is too thick, the wearability is worse. The base weight is more preferably 0.3 mm or more and 1.5 mm or less.

Also, in order to continuously obtain good electrocardiographic waveforms, it is necessary to bring the electrode 46 into contact with skin and maintain an attached state. Since a cloth constituting a fiber structure needs to have flexibility in order for the electrode 46 to be continuously attached to skin, the fiber structure is preferably a woven fabric, a knitted fabric, or a nonwoven fabric, and more preferably a knitted fabric having higher flexibility. Here, when the electrode 46 is broken or moves during wear because the electrode 46 itself is too flexible, a member for reinforcement may be disposed on a back side of the electrode 46.

In addition, tissues and manufacturing methods of fiber structures represented by knitted fabrics are not particularly limited, but a shape of the electrode 46 is preferably a shape which retains moisture such as sweat and double knits can be preferably used as the knitted fabric. Examples of such tissues include double raschel tissues, cardboard tissues, reversible tissues, smooth tissues, milling tissues, fleeced tissues, and the like, but the present invention is not limited thereto.

Woven or knitted fabrics used for the electrode 46 of the present invention preferably include multifilament yarns composed of a plurality of monofilaments in view of supporting of a conductive resin in a fiber structure and high conductivity. Fineness of the multifilament yarns is not particularly limited, but the fineness thereof is preferably 30 dtex to 400 dtex in view of taking advantage of characteristics of the fiber structure. The mixing ratio of multifilament yarns in the woven or knitted fabric is not particularly limited as long as the mixing ratio does not affect performance of the fiber structure, but the mixing ratio thereof is preferably a higher mixing ratio in view of conductivity and durability and more preferably 50% or more and 100% or less.

Examples of materials of the multifilament yarn used for the woven or knitted fabric include polyester-based synthetic fibers such as polyethylene terephthalate, polytrimethylene terephthalate, and polybutylene terephthalate, and polyamide-based synthetic fibers such as nylon, and the like, but the present invention is not limited thereto. Furthermore, materials obtained by blending additives such as titanium oxide into the woven or knitted fabric may be used and fibers modified with polymers used to give functionality such as hygroscopicity improvement may also be used.

Also, cross-sectional shapes of unit monofilaments constituting multifilaments are not limited, and yarns with various different cross-sectional shapes represented by circular shapes, triangular shapes, octagonal shapes, flat shapes, and Y shapes can also be used. As non-elastic yarns, core sheaths or side-by-side type composite yarns composed of polymers with different viscosities can also be used. False twisted yarns obtained by performing false twisting on raw yarns may also be used. Synthetic fibers of polyacrylonitrile, polypropylene, and the like, regenerated fibers of rayon, polynosic, cupra, and the like, semisynthetic fibers of acetate, triacetate, and the like, and natural fibers represented by silk can be used.

The fiber structure according to the present invention preferably includes multifilaments composed of monofilaments with filament diameters of 0.2 dtex or less in view of supporting of conductive resins on fiber surfaces and in voids between fibers. The mixing ratio of the monofilament multifilaments of 0.2 dtex or less in the fiber structure is not particularly limited as long as the mixing ratio does not affect performance of the fiber structure, but the mixing ratio is preferably a high mixing ratio in view of conductivity and durability and more preferably 50% or more and 100% or less.

In addition, as the number of monofilaments increases, voids formed by a plurality of monofilaments, that is, the sizes of regions carrying conductive resins, decrease, so that performance of supporting conductive resins in a fiber structure increases and excellent high conductivity and washing durability can be obtained because continuity of conductive resins is maintained even when the sizes of portions carrying conductive resins are decreased by decreasing filament diameters.

Microfibers with filaments diameters of 5 μm or less used for artificial leathers, outer materials, or the like are preferably used, and nanofibers with filament diameters of 10 nm or more and 1000 nm or less that have been used in recent years for the purpose of preventing slipping of linings of sports clothes, brassieres, golf gloves, and the like are more preferably used.

Fiber structures including nanofiber staple yarn assemblies prepared from "Nanoalloy (registered trademark)" fibers, monofilament yarn assemblies prepared using an electrospinning method and the like, and nanofibers prepared using a known method can be appropriately used as nanofibers, but fiber structures including multifilament yarns of nanofibers are more desirable.

The multifilament yarns of the nanofibers can be prepared using a known composite spinning method or the like.

For example, nanofiber multifilament yarns, in which variations in fiber diameters are small, obtained by performing sea component removal treatment on composite fibers using a composite spinneret disclosed in Japanese Examined Patent Application, First Publication No. 2013-185283 can be effectively used, but the present invention is not limited thereto. Here, the sea component removal treatment refers to a process of melting sea components of fibers and leaving island components.

As the conductive polymers, conductive polymers containing a mixture of poly3,4-ethylenedioxythiophene and polystyrene sulfonic acid (PEDOT-PSS) can be appropriately used.

Besides this, examples of the conductive polymers include pyrrole-based, thiophene-based, isothianaphthene-based, phenylene-based, acetylene-based, and aniline-based conductive polymers, copolymers thereof, or the like. In addition, examples of dopants of the conductive polymers may be at least one type of ion of polymer ions such as halide ions, perchlorate ions, tetrafluoroborate ions, hexafluoroarsenate ions, sulfate ions, nitrate ions, thiocyanate ions, phosphate ions, trifluoroacetate ions, tosylate ions, alkylsulfonate ions, and polyacrylate ions.

The electrode 46 having the fiber structure according to the present invention has low irritation and high safety when in contact with skin. When a signal cannot be obtained satisfactorily due to drying of skin or the like, it is desirable to apply a small amount of physiological saline or humectant to the fiber structure. Examples of the humectant include glycerol, sorbitol, polyethylene glycol, polyethylene glycol-polypropylene glycol copolymers, ethylene glycol, sphingosine, phosphatidylcholine, and the like, and one of these may be independently used or two or more of these may be used in combination.

By moisturizing the electrode 46 as described above, when the electrode 46 comes into contact with skin of a user (a living body) P, an adhesive force occurs due to wettability of the humectant.

The size or a shape of the electrode 46 is not particularly limited as long as a biological signal can be detected and vertical and horizontal lengths are preferably 2 cm or more and 20 cm or less. When the vertical and horizontal lengths of the electrode 46 are less than 2 cm, since an area of the electrode 46 is too small, the electrode 46 is also easily deviated and easily picks up noise when garments move during exercise or the like. When the vertical and horizontal lengths thereof exceed 20 cm, since it is not the size required for actual signal detection and the area of the electrode 46 is too large, an interval between neighboring electrodes is small, which easily causes trouble such as short-circuiting.

Figure 4:
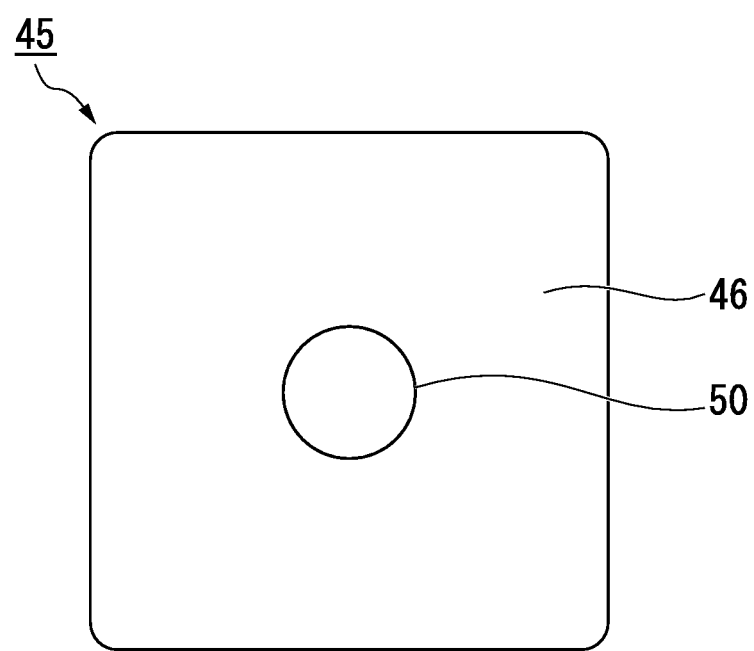
FIG. 4 is a bottom view of the electrode unit.

The vertical and horizontal lengths thereof are more preferably 2.5 or more and 18 cm or less. As shown in FIG. 4, for example, an electrode having a square shape of about 4 cm×about 4 cm and a shape with rounded corners is more preferably used.

The waterproof layer 47 is a layer through which liquid moisture does not pass.

The waterproof layer 47 mentioned herein is not necessarily required and is preferably stacked on one surface of a fiber structure containing a conductive substance as a resin layer. It is desirable to stack a resin layer on a back surface side of a surface coming into contact with a skin side of a fiber structure used for the electrode 46 in consideration of applications to a living body electrode. When a biological signal is detected, it is difficult to detect the biological signal stably when the electrode 46 dries.

Therefore, because it is necessary to maintain the electrode 46 in a wet state to some extent, one surface of the electrode 46 is covered with a resin layer so that drying thereof can be prevented and thus conductivity can be stably obtained. In addition, one surface of the electrode 46 is covered with a resin layer so that falling-off of a conductive resin during washing can be reduced and thus washing durability can be significantly improved.

The type and the shape of a polymer constituting the resin layer are not particularly limited as long as the polymer is a polymer through which a liquid does not pass, and for example, a method of laminating a polymer film of acryl, vinyl chloride, or the like, a method of coating acrylic resins or urethane resins, and the like can be provided. Although a polymer layer is not particularly limited, when it is necessary to moderately control a feeling of stickiness in the skin, the polymer layer is preferably a waterproof moisture-permeable layer.

Examples of the waterproof moisture-permeable layer include forms obtained by stacking polytetrafluoroethylene (PTFE) porous membranes, non-porous membranes made of hydrophilic elastomers such as hydrophilic polyester resins and polyurethane resins polyurethane resin microporous membranes, or the like, known membranes, films, stacked articles, resins or the like using a coating or laminating method, but the present invention is not limited thereto. The waterproof layer 47 is preferably bonded in a stacked manner by laminating a polyurethane resin microporous membrane with stretchability in view of followability to a fiber structure which is a base material. In addition, in order to improve moisture permeability, microporosity may be formed in a fiber structure obtained by stacking a resin layer on one surface thereof using a punching machine or a sewing machine.

The electrode 46 of the electrode unit 45 comes into contact with the user P clothed in the undergarment 10 and acquires an electric biological signal emitted by the user P as will be described below.

A male button (a locking section) 49 is provided in the electrode unit 45. The male button 49 has a known constitution and includes a post 50 and a stud 51. The post 50 and the stud 51 are formed of materials having conductivity such as stainless steel. The post 50 is disposed on the electrode 46 side and the stud 51 is disposed on the waterproof layer 47 side. A part of the post 50 is embedded in the electrode 46 and a part of the stud 51 is embedded in the waterproof layer 47. For this reason, a step formed by the electrode 46 and the post 50 and a step formed by the waterproof layer 47 and the stud 51 decrease.

For example, a head section (a convex section) 50a provided on the post 50 protrudes to the outside via the stud 51. The post 50 and the stud 51 are electrically connected to each other. The male button 49 is provided near center portions of the electrode 46 and the waterproof layer 47. The male button 49 is electrically connected to the electrode unit 45.

The male button 49 is mechanically connected to the undergarment 10 and the electrode unit 45, supports a portion near a center portion of the electrode unit 45 at one point, and electrically connects the electrode unit 45 to a measuring device (a processing device) D via a female button 39 which will be described below.

Figure 5:
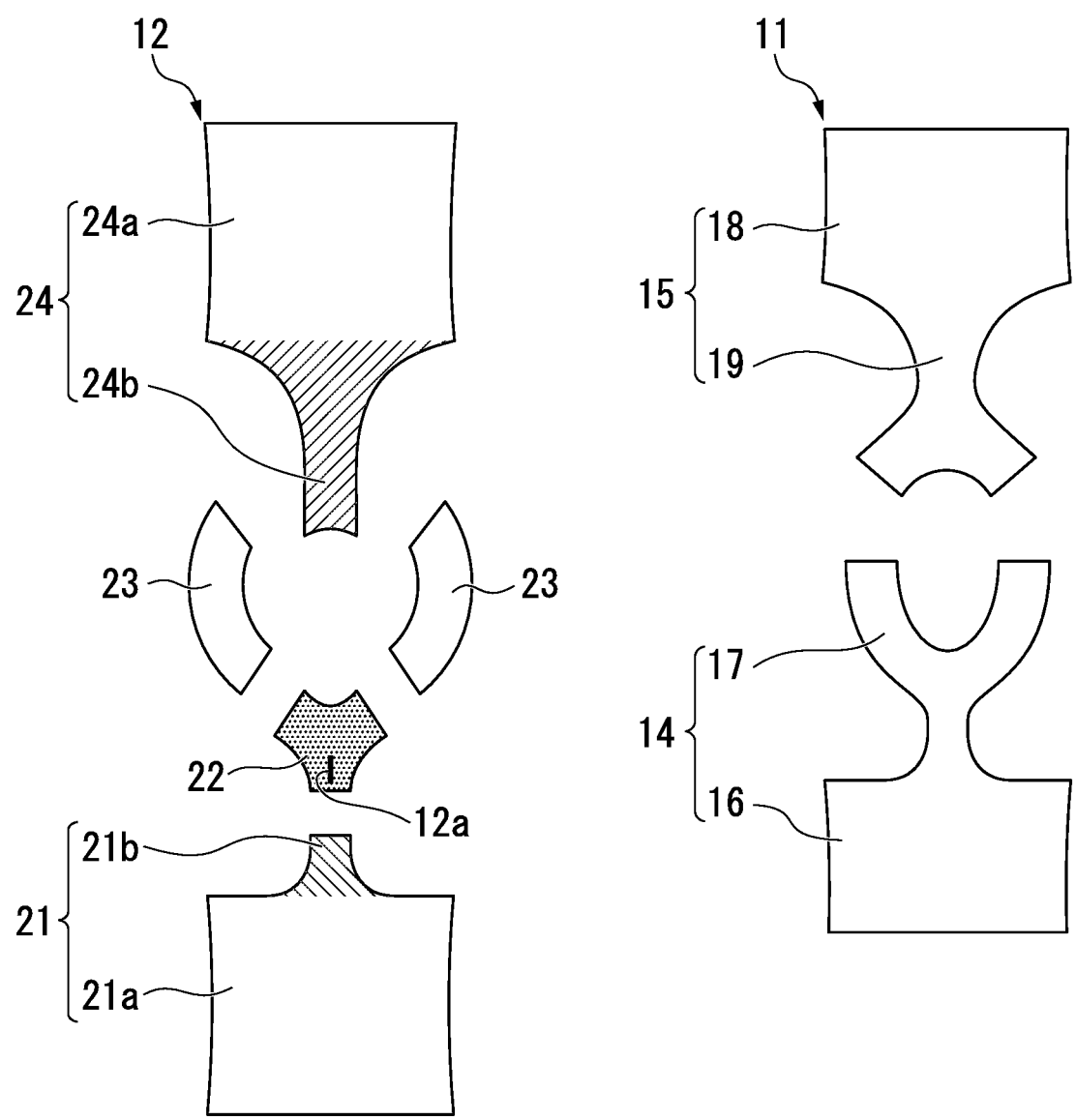
FIG. 5 is a cutting pattern diagram of an outer member and a backing member of the wearable electrode.

As shown in FIG. 5, the outer member 11 is formed by stitching a front body 14 and a back body 15. The front body 14 includes a front body main body 16 formed in a rectangular shape and disposed on a lower portion when the user P is clothed in the undergarment 10 and a front body neckline section 17 formed in Y shape and disposed on an upper portion. The back body 15 includes a back body main body 18 formed in a rectangular shape and disposed on a lower portion when the user P is clothed in the undergarment 10 and a back body neckline section 19 formed in a Y shape and disposed on an upper portion.

The backing member 12 is formed by stitching a front body 21, a back center (a sandwiched part) 22, a pair of back shoulders 23, and a back body 24. The front body 21 is formed in a shape in which a belt-like section 21b protrudes outward from a center portion of one side of a front body main body 21a formed in a rectangular shape. Note that the belt-like section 21b and a belt-like section 24b which will be described below are hatched.

The back body 24 is formed in a shape in which the belt-like section 24b protrudes outward from a center portion of one side of a back body main body 24a formed in a rectangular shape like the front body 21.

A back center 22 is formed in a Y shape. The back shoulders 23 are formed in a C shape.

An area of one surface of the back center 22 is 100 cm² or more and 200 cm² or less.

Figure 6:
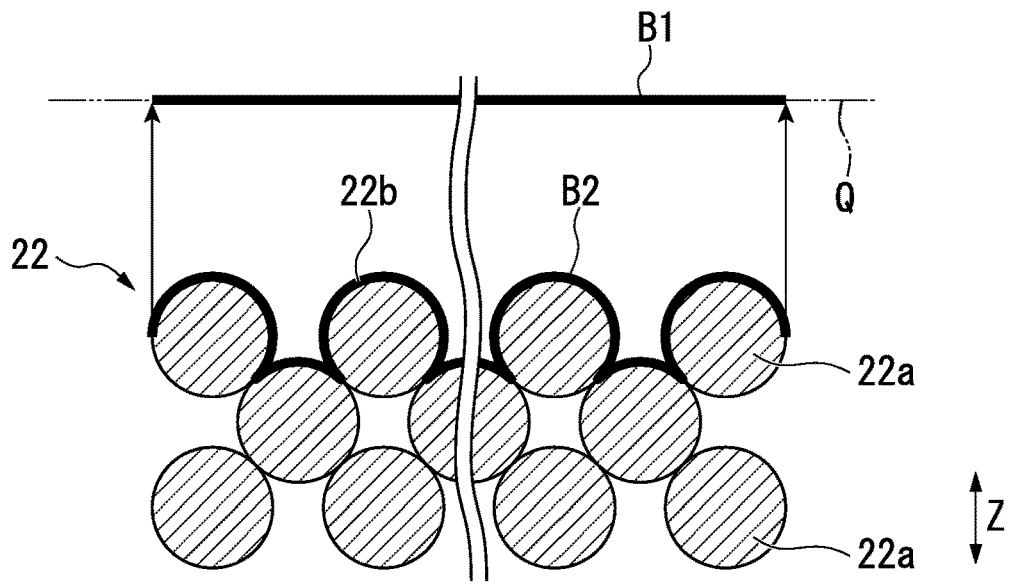
FIG. 6 is a cross-sectional view of a back center of the wearable electrode in a Z direction thereof.

The area of the one surface mentioned herein will be described using FIG. 6. The back center 22 is formed, for example, by weaving fibers 22a. A plane Q which is perpendicular to a thickness direction Z of the back center 22 is defined. In the present specification, an area of one surface 22b of the back center 22 refers to an area B1 obtained by projecting the one surface 22b of the back center 22 in the thickness direction Z and projecting the one surface 22b onto the plane Q. The area of the one surface 22b of the back center 22 does not refer to an area B2 of surfaces of the fibers 22a on the one surface 22b side.

The outer member 11 and the backing member 12 can be formed of fabric or the like. The cloth of the backing member 12 and the outer member 11 may differ.

Elongation percentages of the back center 22 in vertical and horizontal directions measured based on the regulations of a JIS L 1096 8.16.1 A method are smaller than elongation percentages of parts of the backing member 12 other than the back center 22, that is, the front body 21, the back shoulders 23, and the back body 24. The elongation percentages of the back center 22 in the vertical direction and the horizontal direction thereof measured based on the regulations of the JIS L 1096 8.16.1 A method are preferably 15% or less.

With a constitution of the back center 22, a wear pressure required when the undergarment 10 having the backing member 12 is worn and an electrocardiogram is measured can be secured. Note that, when an area of one surface of the back center 22 is larger than 200 cm², the wearability is worse, and when the area of one surface of the back center 22 is less than 100 cm², there is no effect of securing of a wear pressure when the backing member 12 is worn.

The widths of parts of the front body 14 of the outer member 11 and the front body 21 of the backing member 12 having the narrowest body width are preferably 12 cm or less. When the widths thereof exceed 12 cm, a cloth is easily pulled due to an influence of expansion and contraction of the skin when he or she swings his or her arms. As a result, it is undesirable because the electrode unit 45 easily shifts with respect to the skin.

The widths of parts of the back body 15 of the outer member 11 and the back body 24 of the backing member 12 having the narrowest body width are preferably 17 cm or less. When the widths thereof exceed 17 cm, a cloth is easily pulled due to an influence of expansion and contraction of the skin when the user swings his or her arms. As a result, it is undesirable because the electrode unit 45 easily shifts with respect to the skin.

As shown in FIG. 1, an outer member neckline section 11a and a pair of outer member armhole section 11b are formed on the outer member 11 formed by stitching the front body 14 and the back body 15 configured in this way to avoid regions in which movement is relatively larger than other regions when the user P clothed in the undergarment 10 moves his or her neck P3 or arms P4. The regions in which the movement is relatively larger than the other regions mentioned herein include the neck P3 and the arms P4.

Likewise, a backing member neckline section 12c and a pair of backing member armhole sections 12d are formed on the backing member 12 to avoid regions in which movement is relatively larger than other regions when the user P clothed in the undergarment 10 moves his or her neck P3 or arms P4.

A front body neckline section 17 and a back body neckline section 19 sandwiched between the outer member neckline section 11a and the pair of outer member armhole sections 11b are band-like member and formed in a Y shape. The belt-like sections 21b and 24b and the back shoulders 23 sandwiched between a backing member neckline section 12c and the pair of backing member armhole sections 12d are formed in band shapes.

The back center 22 is a part sandwiched between the backing member neckline section 12c and the pair of backing member armhole sections 12d in a part of the backing member 12 which is the front of the user P clothed in the undergarment 10. The back center 22 faces the manubrium sterni (a part between the pair of clavicles) of the user P clothed in the undergarment 10.

An inner diameter L1 of an arm hole section of the outer member 11 and an inner diameter L2 of an arm hole section of the backing member 12 when the user P is clothed in the undergarment 10 are 24 cm or more.

In the outer member 11 and the backing member 12, the body width of the back center 22 is the narrowest.

Figure 7:
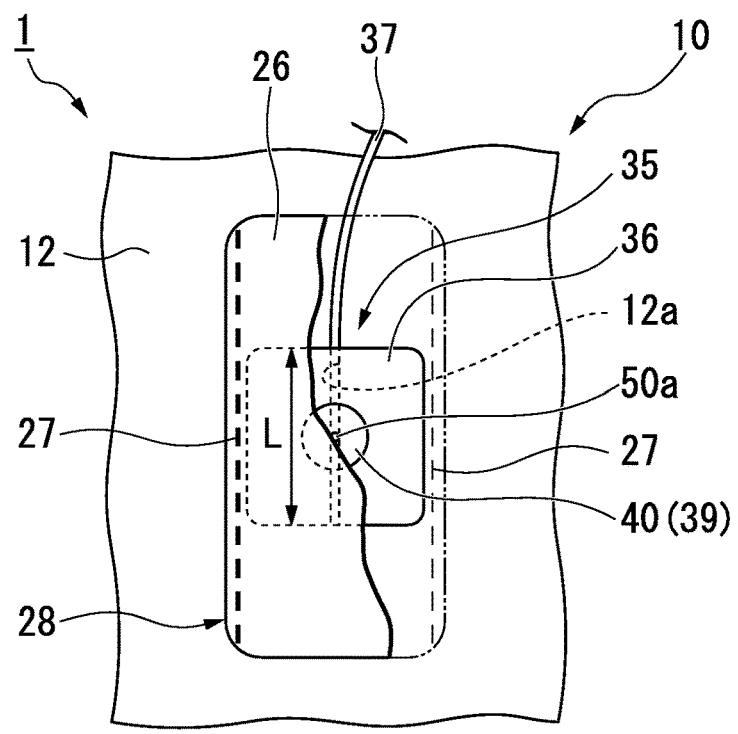
FIG. 7 is a diagram viewed in a direction indicated by an arrow A1 in FIG. 2.

As shown in FIGS. 2 and 7, a slit 12a extending in a vertical direction is formed in the backing member 12. Note that, in FIG. 7, the outer member 11 is not illustrated, and a reinforcing fabric 26, a part of which is cut and which will be described below, is illustrated.

The slit 12a passes through the backing member 12 in a thickness direction. A length L in a vertical direction of the slit 12a is preferably shorter than a length of a short side of the electrode unit 45. For example, when the electrode 46 is a 4 cm square, the length thereof is preferably less than 4 cm (refer to FIG. 7). The width of the slit 12a is not particularly limited as long as a head section 50a of the post 50 is movable along the slit 12a, but an outer diameter of the head section 50a is preferably about an outer circumference of the head section 50a. The head section 50a inserted into the slit 12a is movable in a vertical direction along the slit 12a.

The slit 12a is preferably formed in a position facing a chest P1 of the user P when the user P is clothed in the undergarment 10 with the wearable electrode 1.

As shown in FIG. 1, the outer member 11 and the backing member 12 are formed in tubular shapes. The backing member 12 covers at least a part of an inner surface of the outer member 11.

The outer member 11 and the backing member 12 are formed in a shape which avoids regions such as muscles interlocked by movement of the neck P3 or the arms P4.

The reinforcing fabric 26 may be provided between the backing member 12 and the outer member 11. For example, the reinforcing fabric 26 is formed in a rectangular shape using desired fabrics or the like. The reinforcing fabric 26 is disposed to cover the slit 12a of the backing member 12. The backing member 12 and the reinforcing fabric 26 are connected, for example, by a pair of stitches 27 formed by stitching the backing member 12 and the reinforcing fabric 26 using threads. The stitches 27 extend in a vertical direction and are formed to be away from each other. The backing member 12, the slit 12a, the reinforcing fabric 26, and the pair of stitches 27 configured in this way constitute tubular structures 28.

In this example, the plurality of tubular structures 28 are formed on the backing member 12. The tubular structures 28 are disposed in positions based on any of a national aeronautics and space administration (NASA)'s lead, a CM5 lead, a CC5 lead, and a chest lead C1-6 (hereinafter referred to as a "NASA's lead"). Since the electrode unit 45 is attached through the slit 12a as will be described below, each of the electrode unit 45 is disposed in a position based on the NASA'S lead or the like.

As shown in FIG. 2, the outer member 11 and the backing member 12 are connected by a connection section 30 such as stitches provided above the reinforcing fabric 26. In other words, the outer member 11 and the backing member 12 are connected to each other in a part other than the slit 12a which is a part to which the electrode unit 45 is attached in the backing member 12 as described below. As described below, the electrode unit 45 is attached to the backing member 12 via the slit 12a. It is assumed that a part which is closest to the slit 12a in a part which is connected to the backing member 12 and the outer member 11 is the connection section 30. The connection section 30 is away from the slit 12a of the backing member 12 and is preferably 1 cm or more away therefrom.

An annular loop section (a wire holding section) 31 may be provided on the backing member 12 above the slit 12a.

Note that, although the loop section 31 is provided in the backing member 12 above the slit 12a in the embodiment, the loop section 31 may be provided on the outer member 11 above the slit 12a.

As shown in FIGS. 2 and 7, the wiring section 35 includes a support plate 36 disposed in one of the tubular structures 28 and a connection wiring 37 having a first end portion connected to the support plate 36.

The support plate 36 is formed in a rectangular shape using a desired resinous plate material, a fabric, or the like. The support plate 36 preferably has certain rigidity to be able to easily move in the tubular structures 28. The width of the support plate 36 is shorter than a distance between the pair of stitches 27. The support plate 36 is vertically movable in the tubular structures 28 using the pair of stitches 27 as guides.

The position of the support plate 36 in a vertical direction is maintained by a frictional force occurring between the support plate 36 and the backing member 12 and the reinforcing fabric 26.

A female button (a locked section) 39 is provided near a center portion of the support plate 36 of the wiring section 35. A dot button 38 is constituted of the male button 49 and the female button 39.

The female button 39 is of a known constitution provided in the underwear 10 and includes a head 40 and a socket 41.

The head 40 and the socket 41 are formed of materials with conductivity such as stainless steel. The head 40 is disposed on the reinforcing fabric 26 side and the socket 41 is disposed on the backing member 12 side. The head 40 and the socket 41 are electrically connected to each other. For example, a concave section 40a which is detachably locked to the head section 50a of the post 50 is provided in the head 40. Note that, in the embodiment, it is assumed that the concave section 40a also has a shape of a hole passing through the head 40. The female button 39 is electrically connected to the connection wiring 37 of the wiring section 35.

The head section 50a of the male button 49 inserted into the slit 12a of the backing member 12 can be locked to the concave section 40a of the female button 39. In other words, the female button 39 and the male button 49 disposed to sandwich the slit 12a are locked to each other to be integrated and vertically move along the slit 12a (the pair of stitches 27).

When the male button 49 and the female button 39 are locked to each other, the male button 49 and the female button 39 are electrically connected to each other.

As the connection wiring 37, a well-known wiring such as a so-called flexible wiring can be appropriately selected and used. A core wire (not shown) of the connection wiring 37 is electrically connected to the female button 39. The connection wiring 37 is drawn upward from the female button 39, passes through the loop section 31, and then is routed downward. In other words, the loop section 31 holds the connection wiring 37.

A second end portion of the connection wiring 37 is connected to the measuring device D.

The measuring device D has a known constitution capable of processing an electric biological signal emitted by the user P.

As shown in FIG. 1, for example, the measuring device D is held in an accommodation section 12b such as a pocket provided in the backing member 12. The measuring device D may be held in an accommodation section provided in the outer member 11, a waist bag attached to the user P, or the like.

An action of the wearable electrode 1 configured as described above will be described below.

The user P performs washing or the like of the underwear 10 obtained by removing the wiring section 35 and the electrode unit 45. The support plate 36 of the electrode unit 45 is inserted into each of the tubular structures 28 of the underwear 10. The head section 50a of the male button 49 is inserted into the slit 12a of the backing member 12 and the head section 50a of the male button 49 is locked to the concave section 40a of the female button 39 so that the male button 49 is locked to the female button 39. The wearable electrode 1 is constituted by placing the measuring device D in the accommodation section 12b. At this time, the female button 39 and the male button 49 are electrically connected to each other.

When the user P is clothed in the underwear 10 of the wearable electrode 1, the electrode 46 of the electrode unit 45 comes into contact with skin or the like of the chest P1 of the user P. Since the electrode 46 is easily deformed, the electrode 46 is easily deformed in accordance with a shape of the chest P1 or the like and thus a biological signal emitted by the user P is easily acquired using the electrode 46. Since moisture passes through the waterproof layer 47 when the waterproof layer 47 is set to be a waterproof moisture-permeable layer, the chest P1 or the like is not easily warmed up.

The underwear 10 covers a part of at least one of ribs, costal cartilage, sternum, and clavicles of the user P.

Here, the electrode unit 45 attached to the back center 22 of the backing member 12 and disposed to face the chest P1 of the user P, more specifically, manubrium sterni (a part between a pair of clavicles) is particularly referred to as a electrode unit 45a (refer to FIG. 1).

Since the electrode unit 45 is attached to the backing member 12, the electrode unit 45 hardly floats from the chest P1 of the user P.

Since the electrode unit 45a is attached to the back center 22 of the backing member 12 and is drawn from three direction by the back shoulders 23 and the belt-like section 21b which are band-like members, the electrode unit 45a particularly hardly floats from the chest P1.

A sticking effect of the electrode unit 45 to skin due to wettability and viscosity thereof is stabilized when the following four conditions are satisfied. Firstly, the electrode unit 45 is brought into contact with skin in parallel (flat). Secondly, the electrode unit 45 is supported at a portion near a center portion of the electrode unit 45 and is pressed toward skin. Thirdly, the electrode unit 45 is not deviated (not shifted) on skin. Fourthly, humectants is not let be lost (by dry diffusion or the like).

Examples of factors causing failure or interruption of measurement due to the above-described four conditions include a force (horizontal and vertical forces) of peeling off the electrode unit 45 from a skin surface, skin deformation due to movement of a body, and loss of humectants (due to drying or the like). The force of peeling off the electrode unit 45 and the skin deformation due to the body movement lead to poor contact between skin and the electrode unit 45. Loss of humectants leads to an increase in contact resistance between skin and the electrode unit 45. Particularly, measurement is impaired due to large movement of his or her body, the connection wiring 37 of the electrode unit 45, and pulling by an underwear in the related art in many cases.

The user P appropriately moves the electrode unit 45 in a vertical direction according to necessity to adjust the position of the electrode unit 45.

A biological signal acquired using the electrode 46 of the electrode unit 45 is transmitted to the measuring device D via the male button 49, the female button 39, and the connection wiring 37 which are electrically connected to each other.

When the measuring device D starts up, measurement of biological signals of electrocardiographic waveforms or the like is started. The user P performs an operation such as walking while measuring a biological signal.

The outer member 11 of the underwear 10 moves along with the user P's motion in some cases. Since the connection section 30 is away from the slit 12a of the backing member 12, movement of the outer member 11 is suppressed from being transferred to the slit 12a of the backing member 12. For this reason, a state in which the electrode 46 of the electrode unit 45 comes into contact with the chest P1 or the like of the user P is maintained.

When the connection wiring 37 serving as a part near the measuring device D is pulled, a force acting on the connection wiring 37 is received by the loop section 31 and then transmitted to the female button 39. Thus, a force pulling the connection wiring 37 is suppressed from being transmitted to the female button 39. The electrode unit 45 is not pulled downward due to a weight of the connection wiring 37 and adhesion of the electrode unit 45 to skin can be enhanced.

Also, the outer member neckline section 11a and the pair of outer member armhole section 11b are formed on the outer member 11 and the backing member neckline section 12c and the pair of backing member armhole sections 12d are formed on the backing member 12. For this reason, even when the user P moves the neck P3 or the arms P4, the outer member 11 and the backing member 12 hardly move due to this movement.

The back center 22 is formed of a material which is harder than and does not easily stretch compared to those of the front body 21, the back shoulders 23, and the back body 24. For this reason, stretching of the back center 22 is suppressed even when the underwear 10 moves and thus the electrode unit 45a is not easily separated from the skin of the chest P1.

As described above, according to the wearable electrode 1 of the embodiment, when the outer member 11 of the underwear 10 worn by the user P moves, since the slit 12a and the connection section 30 are provided in different parts of the backing member 12, the movement of the outer member 11 is hardly transmitted to the electrode unit 45 via the connection section 30. Therefore, movement of the electrode unit 45 can be suppressed.

It is difficult for an electrode to float up or deviate even when the chest P1 is twisted or bent forward and thus a biological signal can be stably acquired.

Also, the electrode 46 formed of a conductive fiber structure is characterized by having almost no discomfort during wearing and being suitable for long-term measurement. Since a stable contact state to skin can be maintained as long as an adhesive force is not lost, long-term measurement of a biological signal is possible.

The wiring section 35 does not easily direct come into contact with skin by sandwiching the wiring section 35 between the outer member 11 and the backing member 12.

The male button 49 is provided on the electrode unit 45, the female button 39 is provided in the wiring section 35, and the head section 50a of the male button 49 is inserted into the slit 12a formed in the backing member 12. The male button 49 and the female button 39 which are locked to each other can move along the slit 12a. Therefore, the position of the electrode unit 45 with respect to the underwear 10 can be adjusted.

The wearable electrode 1 includes the loop section 31 so that a force when the loop section 31 is pulled is received by the loop section 31. Therefore, transmitting of the pulled force to the female button 39 can be suppressed.

The outer member neckline section 11a and the pair of outer member armhole section 11b are formed on the outer member 11 and the backing member neckline section 12c and the pair of backing member armhole sections 12d are formed on the backing member 12. In other words, the underwear 10 is shaped to cover an upper chest to avoid the neck P3 and the arms P4. Therefore, since there is no pressure on the entire chest P1, he or she does not almost feel a pressure on his or her chest due to tightening.

Since the outer member 11 and the backing member 12 are formed in a shape configured to avoid regions such as muscles interlocked by movement of the neck P3 or the arms P4, the outer member 11 and the backing member 12 does not easily move even when the neck P3 or the arms P4 moves. As a result, the electrode unit 45 hardly floats from the chest P1 of the user P.

Since an elongation percentage of the back center 22 is smaller than an elongation percentage of the front body 21 or the like, a biological signal can be acquired more reliably using the electrode unit 45a even when the underwear 10 moves relative to the user P or the user P himself or herself moves.

Although the embodiment of the present invention has been described in detail above with reference to the drawings, a specific constitution is not limited to such an embodiment and also includes a design or the like within the scope which does not depart from the gist of the present invention.

For example, in the embodiment, it is assumed that the male button 49 as a locking section is electrically connected to the electrode unit 45 and the female button 39 as a locked section is electrically connected to the wiring section 35.

However, a male button as a locking section may be electrically connected to the wiring section 35 and a female button as a locked section may be electrically connected to the electrode unit 45.

It is assumed that a wire holding section is the loop section 31 which holds the connection wiring 37 when the connection wiring 37 of a wiring section passes through the loop section 31. However, the wire holding section may be a knot or the like formed of a yarn which holds the connection wiring 37 by fixing the backing member 12 and the connection wiring 37 to the wire holding section itself.

Note that, when a length of the connection wiring 37 is short, or the like, the wearable electrode 1 may not include the loop section 31.

It is assumed that the measuring device D configured to display an electrocardiogram is electrically connected to an end portion of the connection wiring 37. However, a device connected to the connection wiring 37 is not limited thereto and may be, for example, a device capable of performing processing such as detection and display of a biological signal and a device configured to transmit a biological signal to an external device through wireless communication or the like.

INDUSTRIAL APPLICABILITY

According to the present invention, a wearable electrode, movement of an electrode unit of which is suppressed, can be provided even when a garment worn a user moves.

REFERENCE SYMBOLS

1 Wearable electrode
10 Underwear (garment)
11 Outer member
11a Outer member neckline section
11b Outer member armhole section
12 Backing member
12a Slit
12c Backing member neckline section
12d Backing member armhole section
14, 21 Front body
15, 24 Back body
22 Back center (sandwiched part)
35 Wiring section
39 Female button (locked section)
40a Concave section
45 Electrode unit
49 Male button (locking section)
50a Head section (convex section)
P User (living body)

The invention claimed is:

1. A wearable electrode comprising:
  a garment including:
    an outer member comprising an outer member neckline section and a pair of outer member armhole sections forming a Y-shape and adapted to be positioned on a user to avoid regions in which movements influenced thereto is relatively larger than other regions when a user clothed in the garment moves his or her neck or arms,
    a backing member comprising a backing member neckline section and a pair of backing member armhole sections forming a Y-shape and adapted to be positioned on the user to avoid the regions in which movements influenced thereto is relatively larger than the other regions when the user clothed in the garment moves his or her neck or arms; and a back center surrounded by the backing member neckline section and the pair of backing member armhole sections and adapted to be positioned in front of the user; and
  a wiring section disposed between the outer member and the backing member, the wiring section comprising:
    an electrode unit attached to the back center on an opposite side of the inner surface of the outer member and adapted to acquire a biological signal from the user, wherein the outer member and the backing member are connected to each other by stitches and provided above a part of the backing member to which the electrode unit is attached;
  a flexible connection wiring electrically connected to the electrode unit;
  a locking section having a convex section and is electrically connected to the electrode unit;
  a locked section having a concave section and is electrically connected to the flexible connection wiring, the locked section is detachably locked to the convex section and when the locking section and the locked section are locked to each other, the locking section and the locked section are electrically connected to each other;
  a slit formed in the backing member and the convex section of the locking section being configured to be inserted into the slit;
  a wire holding section having a loop, wherein the loop is attached above the slit to either the outer member or the backing member and is spatially separated from the electrode unit; and
  wherein the flexible connection wiring is electrically connected to the locked section and the wiring section at a first end of the flexible connection wiring, the flexible connection wiring being drawn upward from the locked section, passing through the loop of the wire holding section, and then being routed downward from the loop of the wire holding section so that a second end of the flexible connection wiring is connected to a measuring device.

2. The wearable electrode according to claim 1, wherein elongation percentages of the back center adapted to face a manubrium sterni and located between a pair of clavicles of the user is smaller than elongation percentages of parts of the backing member other than the back center when the user is clothed in the garment.

3. The wearable electrode according to claim 1, wherein the back center is adapted to face a manubrium sterni located between a pair of clavicles of the user when the user is clothed in the garment.

* * * * *